(12) United States Patent
Rosati et al.

(10) Patent No.: US 8,404,279 B2
(45) Date of Patent: Mar. 26, 2013

(54) METHOD FOR IMPROVING THE BUD QUALITY OF A PLANT

(75) Inventors: Dominique Rosati, Neyron (FR); Luk De Maeyer, Orsmaal-Linter (BE); Piet Creemers, Sint-Truiden (BE); Hilde Schoofs, Halen (BE); Tom Deckers, Bekkevoort (BE)

(73) Assignee: Bayer CropScience AG, Monheim (DE)

( * ) Notice: Subject to any disclaimer, the term of this patent is extended or adjusted under 35 U.S.C. 154(b) by 5 days.

(21) Appl. No.: 12/599,765

(22) PCT Filed: May 16, 2008

(86) PCT No.: PCT/EP2008/056064
§ 371 (c)(1),
(2), (4) Date: Jul. 12, 2010

(87) PCT Pub. No.: WO2008/142029
PCT Pub. Date: Nov. 27, 2008

(65) Prior Publication Data
US 2010/0311590 A1    Dec. 9, 2010

(30) Foreign Application Priority Data

May 16, 2007   (EP) .................................... 07356068

(51) Int. Cl.
*A01N 59/26*   (2006.01)
*A61K 33/42*   (2006.01)

(52) U.S. Cl. ........................................ 424/601; 424/602
(58) Field of Classification Search .................... None
See application file for complete search history.

(56) References Cited

U.S. PATENT DOCUMENTS 6,200,929 B1 * 3/2001 Horibe et al. ................. 504/127
2010/0040656 A1 * 2/2010 Franklin et al. ............... 424/405

FOREIGN PATENT DOCUMENTS

WO   WO 2005/113128   12/2005

OTHER PUBLICATIONS

International Search Report of PCT/EP2008/056064, completed Oct. 6, 2008.
Montesinos et al. "Effect of Bactericides, Phosphonates and Nutrient Amendments on Blast of Dormant Flower Buds of Pear: A Field Evaluation for Disease Control", European Journal of Plant Patholog, vol. 107 (2001) pp. 787-794.
Görlach et al. "Benzothiadiazole, A Novel Class of Inducers of Systemic Acquired Resistance, Activates Gene Expression and Disease Resistance in Wheat", The Plant Cell, vol. 8 (1996) pp. 629-643.

* cited by examiner

*Primary Examiner* — Alton Pryor
(74) *Attorney, Agent, or Firm* — Baker Donelson Bearman Caldwell & Berkowitz, PC

(57) ABSTRACT

The present invention relates to the use of a compound, in particular of a derivative of phosphorous acid, especially of fosetyl-Al, for treating plants for the purpose of improving the bud quality thereof.

15 Claims, No Drawings

METHOD FOR IMPROVING THE BUD QUALITY OF A PLANT

CROSS REFERENCE TO RELATED APPLICATIONS

This application is a §371 National Stage Application of PCT/EP2008/056064 filed May 16, 2008, which claims priority to European Application 07356068.2 filed May 16, 2007.

BACKGROUND OF THE INVENTION

1. Field of the Invention

The present invention relates to the use of a compound, in particular of a derivative of phosphorous acid, especially of fosetyl-Al, for treating plants for the purpose of improving the bud quality thereof.

2. Description of Related Art

Fosetyl-aluminum or fosetyl-Al is a known fungicidal compound. Its chemical name is aluminum ethyl hydrogen phosphonate whose chemical structure is the following:

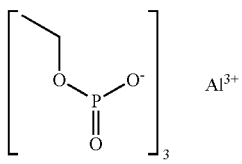

Moreover, the bactericidal activity of fosetyl-Al is also known, especially from European patent application EP-249566.

The problem of flower bud dieback is not new and has already been examined for a long time. For many years, the phenomenon of flower bud dieback, especially on pear trees, has been observed. Such a phenomenon can, within a few years, dramatically reduce the productivity of fruit trees. This phenomenon may also lead to the digging up or destruction of the affected plants in order to avoid the propagation of the organisms implicated.

The origin or the reasons for this phenomenon are not known. It could be linked to bacterial infections, for example caused by *Pseudomonas syringae* pv. *syringae* or alternatively fungal infections, for example caused by *Alternaria alternata*. This phenomenon could also be explained by a late availability of nitrogen which stimulates the physiological activation of flower buds that is not externally perceptible and that could make them more vulnerable to such a flower bud dieback.

Furthermore, the frequency of the flower buds that have died back can vary considerably from year to year and the youngest plants may be more sensitive than the older plants for the same cultivar, the phenomenon may vary from one variety to another. During the season, the climate may also have an influence on the phenomenon; a hot period at the end of the autumn season followed by a period of heavy frost has often been considered as a decisive element which may lead to the dieback of flower buds. It may also happen that the flower buds are not sufficiently in winter dormancy at the time of the first frosts. The internal tissue of the flower buds can thus be damaged and then infected.

The damage caused by dieback of buds is often only visible several months after having been initiated, or even the following year at the time of flowering, of fruit formation or of harvest. It is then impossible to undertake the least treatment aimed at reviving the situation.

Some antibiotic or antibacterial products, such as streptomycin, have been used for combating this phenomenon. Such plant protection uses of products are now limited as far as possible, or even banned, especially because of problems of resistance in the phytopathogenic bacteria which are generated by massive land spreading of such antibiotic or antibacterial products. Such problems of resistance could be transferred to bacteria that are pathogenic for animals or even humans.

SUMMARY OF THE INVENTION

It has now been found that the use, according to the present invention, constitutes a solution to all or some of these problems.

Accordingly, the present invention relates to the use for improving the quality of the buds of a perennial plant by applying a compound to this plant at the time of the period of initiation of the flower buds in the post-flower period.

Preferably, the use according to the present invention uses a compound chosen from pesticidal compounds, especially fungicidal, bactericidal or herbicidal compounds, or plant growth regulators, insecticides or nematicides.

DETAILED DESCRIPTION OF A PREFERRED EMBODIMENT

More preferably, the use according to the present invention uses a compound chosen from:

B1) a compound capable of inhibiting the synthesis of nucleic acids of the RNA type, such as benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;

B2) a compound capable of inhibiting mitosis and cell division, such as benomyl, carbendazim, diethofencarb, ethaboxam, fuberidazole, pencycuron, thiabendazole, thiophanate-methyl, zoxamide;

B3) a compound capable of inhibiting respiration, for example
a respiratory inhibitor CI such as diflumetorim;
a respiratory inhibitor CII such as boscalid, carboxin, fenfuram, flutolanil, furametpyr, furmecyclox, mepronil, oxycarboxin, penthiopyrad, thifluzamide;
a respiratory inhibitor CIII such as amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

B4) a compound acting as a respiratory decoupler such as dinocap, fluazinam, meptyldinocap;

B5) a compound capable of inhibiting the production of ATP such as fentin acetate, fentin chloride, fentin hydroxide, silthiofam;

B6) a compound capable of inhibiting the biosynthesis of proteins and AA biosynthesis such as andoprim, blasticidin-S, cyprodinil, kasugamycin, kasugamycin hydrochloride hydrate, mepanipyrim, pyrimethanil;

B7) a compound capable of inhibiting the signal transmission such as fenpiclonil, fludioxonil, quinoxyfen;

B8) a compound capable of inhibiting the lipid and membrane synthesis such as biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

B9) a compound capable of inhibiting the ergosterol biosynthesis such as aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

B10) a compound capable of inhibiting the synthesis of the cell membrane such as benthiavalicarb, dimethomorph, flumorph, iprovalicarb, mandipropamid, polyoxins, polyoxorim, validamycin A;

B11) a compound capable of inhibiting the biosynthesis of melanin such as carpropamid, diclocymet, fenoxanil, phthalide, pyroquilon, tricyclazole;

B12) a compound capable of inducing the plant defense reactions such as acibenzolar-S-methyl, probenazole, tiadinil;

B13) a compound having a multisite activity such as Bordeaux mixture, captafol, captan, chlorothalonil, copper naphthenate, copper oxide, copper oxychloride, copper-based preparations such as copper hydroxide, copper sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulfur and sulfur preparations such as calcium polysulfide, thiram, tolylfluanid, zineb, ziram;

B14) a compound chosen from the list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy)methyl]-phenyl}-2-(methoxyimino-N-methylacetamide, 1-(4-chlorophenyl)-2-(1H-1,2,4-triazol-1-yl)cycloheptanol, 1-[(4-methoxy-phenoxy)methyl]-2,2-dimethylpropyl-1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3-(difluoromethyl)-1-methyl-N-[2-(1,1,2,2-tetrafluoroethoxy)-phenyl]-1H-pyrazole-4-carboxamide, 3-(difluoromethyl)-N-[(9R)-9-isopropyl-1,2,3,4-tetrahydro-1,4-methanonaphthalen-5-yl]-1-methyl-1H-pyrazole-4-carboxamide, 3-(difluoromethyl)-N-[(9S)-9-isopropyl-1,2,3,4-tetrahydro-1,4-methanonaphthalen-5-yl]-1-methyl-1H-pyrazole-4-carboxamide, 3-(difluoromethyl)-N-[4'-(3,3-dimethylbut-1-yn-1-yl)biphenyl-2-yl]-1-methyl-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-chloro-7-(4-methylpiperidin-1-yl)-6-(2,4,6-trifluorophenyl)[1,2,4]triazolo[1,5-a]pyrimidine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dichloran, difenzoquat, difenzoquat methylsulfate, diphenylamine, ecomate, ferimzone, flumetover, fluopicolide, fluoroimide, flusulfamide, fosetyl-aluminum, fosetyl-calcium, fosetyl-sodium, hexachlorobenzene, irumamycin, isotianil, methasulfocarb, methyl-(2E)-2-{2[({cyclopropyl[(4-methoxy-phenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-(3',4'-dichloro-5-fluoro-biphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(1,3-dimethylbutyl)phenyl]-5-fluoro-1,3-dimethyl-1H-pyrazole-4-carboxamide, N-{(Z)-[(cyclopropyl-methoxy)imino][6-(difluoromethoxy)-2,3-difluorophenyl]methyl}-2-phenylacetamide, N-{2-[1,1'-bi(cyclopropyl)-2-yl]phenyl}-3-(difluoromethyl)-1-methyl-1H-pyrazole-4-carboxamide, N-{2-[3-chloro-5-(trifluoromethyl)pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy]phenyl}-imidoformamide, N-ethyl-N-methyl-N'-{2-methyl-5-(difluoro-methyl)-4-[3-(trimethylsilyl)propoxy]phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, S-allyl-5-amino-2-isopropyl-4-(2-methylphenyl)-3-oxo-2,3-dihdryo-1H-pyrazole-1-carbothioate, tecloftalam, tecnazene, triazoxide, trichlamide, valiphenal, zarilamid.

The following compounds may also be suitable for application according to the invention: bronopol, dichlorophen, nitrapyrin, nickel dimethyldithiocarbamate, kasugamycin, octhilinone, furancarboxylic acid, oxytetracycline, probenazole, streptomycin, tecloftalam.

According to another embodiment of the use according to the invention, several of these compounds may be applied to the perennial plant treated during the post-flower period.

Most preferably, the use according to the present invention uses a compound chosen from phosphorous acid and fosetyl-Al.

Advantageously, the use according to the present invention is used by application starting at the time of initiation of the flower bud of the treated plant. More advantageously still, the use according to the present invention is used by application carried out at the time of initiation of the flower bud and of cell multiplication in the buds.

Equally advantageously, the use according to the present invention is used by application which stops approximately 10 weeks after having started, preferably approximately 8 weeks after having started.

According to a preferred embodiment of the invention, the compound used during the use according to the invention is applied several times during the post-flower period of the plant, at least three applications give particularly advantageous results.

The use according to the present invention also gives very advantageous results when the compound is applied in quantities which make it possible to obtain a concentration, in particular of phosphorous acid, in the plant of 15 ppm, preferably of at least 30 ppm.

According to a particularly advantageous embodiment of the use according to the invention, fosetyl-Al is applied repeatedly, for example three times, in a quantity of at least 1.5 kg/ha, preferably of at least 2 kg/ha, more preferably of at least 3 kg/ha, for example 3.75 kg/ha.

For its use according to the present invention, the compound used is generally applied conventionally as regards its formulation or the type of application. Thus, said compound is generally applied to the aerial parts of the plant, such as the trunk, the stems, the leaves, the fruit or the flowers of said plant.

The use according to the invention may be used on numerous plants and in particular on cotton; flax; vine; fruit or vegetable crops such as *Rosaceae* sp. (for example pome fruit crops such as apple trees, pear trees, but also stone fruit crops such as apricot trees, cherry trees, plum trees, sour cherry trees, almond trees, peach trees); *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana or plantain crops), *Rubiaceae* sp., *Theaceae* sp., *Sterculiceae* sp., *Rutaceae* sp. (for example lemon, orange or grapefruit crops); vegetable crops, *Umbelliferae* sp., *Cruciferae* sp., *Chenopodiaceae* sp., *Cucurbitaceae* sp., *Rosaceae* sp. (for example strawberries); industrial or cereal crops; *Solanaceae* sp. (for example potato) *Chenopodiaceae* sp.; horticultural, tree and forestry crops; *Ericaceae* sp. (for example rhododendron); *Azalea* sp.; and genetically modified homologs of these crops. Such genetically plants are plants whose genome comprises a heterologous gene encoding a protein of interest has been stably inserted. A heterologous gene encoding a protein of interest mainly makes it possible to provide the modified plant with new agronomic properties or to improve the agronomic qualities of this modified plant.

Preferably, the use according to the invention is used on fruit crops, for example, pome fruit crops such as apple trees, pear trees but also stone fruit crops such as apricot trees, cherry trees, plum trees, sour cherry trees, almond trees, peach trees.

The quantity of compound used for the use according to the invention may vary, in particular because of the pathogens targeted, the type of crop, the climatic conditions and according to the actual type of compound used. This quantity may for example be determined by systematic field trials, within the ability of persons skilled in the art.

It is important that the quantity used is effective but also that it is not phytotoxic for the treated plant. Thus, such a quantity should not cause any notable symptom of phytotoxicity on said plant.

According to the compound used, the quantity used for the use according to the invention may generally range from 2 to 8000 g/ha, preferably from 20 to 4000 g/ha.

The use according to the invention is now illustrated by a particular example whose sole objective is to give a particular embodiment of this use without limiting the scope or extent thereof.

EXAMPLE 1

Use Against Flower Bud Dieback on Pear Trees (Conference Variety)

Introduction

During a consecutive period of three years, a study was carried out on young pear trees (cultivar of Conference pears) in a sensitive orchard.

Materials and Method

During three consecutive years 2004, 2005 and 2006, a trial was carried out on young pear trees of the Conference cultivar on a Quince Adams stock. The pear trees of this orchard were planted in 1999 according to the system of a single row at a planting distance of 3.5 m between the rows and 1.5 m in the row with a tree height of 3 m.

During the 2004 trial, three products were compared in an arbitrary block design with 10 trees per plot in four repeats: the observations were made on the 8 trees inside the plot. In 2004, the following products were included in this trial: fosetyl-Al (Aliette product) at a dose varying between 2 and 3.75 kg/ha of standard orchard (corresponding to a dose varying from 1.33 to 2.50 kg/ha of foliar surface area), benzothiadiazole (Bion product) at a dose of 200 g/ha of standard orchard (corresponding to a dose of 133 g/ha of foliar surface area in order to take into account the application volume) and potassium phosphonate (or phosphorous acid) at two doses: one of 11.25 l/ha of standard orchard (corresponding to a dose of 7.50 l/ha of foliar surface area) with the intention to apply the same quantity of phosphonate per ha as in the plot treated with fosetyl-Al applied at 3.75 kg/ha and at a lower dose of 3.00 l/ha of standard orchard (corresponding to a dose of 2.00 l/ha of foliar surface area). The applications were in the post-flower period at an interval of 10 days.

In 2005, the same applications were repeated on the same trees. Because of some phytotoxicity observed after the applications in 2004, the treatments with potassium phosphonate were not repeated.

In 2006, the complete trial was repeated on new trees in the same orchard. The fosetyl-Al doses varying between 2 and 3.75 kg/ha of standard orchard (corresponding to doses varying from 1.33 to 2.50 kg/ha of foliar surface area) were applied in the post-flower period during the months of May and June at an interval of 5 or 10 days between the treatments. Benzothiadiazole applied at a dose of 200 g/ha of standard orchard (corresponding to a dose of 133 g/ha of foliar surface area) was included as reference product in order to induce plant defense reactions by the trees.

After one year during flowering, the effect of the treatments on the quality of the flower bud was evaluated. Statistical analysis of the various parameters is performed (Unistat Statistical Package, Version 5.5). The original or processed data are analyzed according to the General Linear Model and the treatment means are separated in a standard manner using the Duncan multiple classification test (5% level).

In 2006, the magnitude of the levels of fosetyl-Al and phosphorous acid residues in the developing flower buds was monitored on three plots: in the control untreated plot, in the plot treated with fosetyl-Al based on 3×3.75 kg/ha (application on 18/05, 30/05 and 08/06) and in the plot treated with fosetyl-Al based on 6×2.0 kg/ha (application on 18/05, 30/05, 08/06, 19/06, 29/06 and 10/07).

On each date (with the exception of the first sampling date), 40 flower buds with their surrounding leaves were gathered. On the first sampling date, 40 flower buds were gathered without leaves.

The flower bud samples were taken before the next treatment on the following dates: 30/05, 08/06, 19/06, 28/06, 10/07 and 28/08. For the two fosetyl-Al and phosphorous acid products, the levels of residues in the flower buds were determined with the aid of an LC-MS-MS analytical method. The limit of quantification (LOQ) was 0.1 mg/kg for fosetyl-Al, 2 mg/kg for phosphorous acid and 3 mg/kg for the total residue expressed as fosetyl-Al equivalent. The total residue is the sum of the residues derived from fosetyl-Al and phosphorous acid expressed as fosetyl-Al equivalent.

quality (>88% of good quality buds). The plot treated with fosetyl-Al at 3.75 kg/ha has the best results in terms of efficacy and absence of phytotoxicity, therefore allowing the best optimization of fruit production. The results point to an insufficient activity of the benzothiadiazole used as reference product.

The addition of an additional treatment with fosetyl-Al after harvesting makes it possible to arrive at results comparable with those obtained after the post-flower treatments alone.

Table 1 also presents the number of incomplete flower buds per tree in the plots which received phosphorous acid; these data show a significant reduction in the formation of incomplete flower buds. In the untreated plot, 26 incomplete flower buds were counted per tree, this means flower buds without leaves or with a limited number of flowers per cluster. For the trees which received phosphorous acid, this number was reduced to about 8 incomplete flower buds per tree.

TABLE 1 formation of the 2005 flower bud as a result of the treatments performed in 2004

|  | Number of treatments | Dose (kg/ha) | Time of application | Interval | Buds of good quality | Number of incomplete buds/tree |
|---|---|---|---|---|---|---|
| Not treated | / | / | / | / | 66.4 | 26.1 |
| Fosetyl-Al | 3 | 3.75 | May | 10 | 88.4 | 7.9 |
| Fosetyl-Al + | 3 | 3.75 | May | 10 | 89.3 | 7.9 |
| Fosetyl-Al | 3 | 3.75 | June | 14 |  |  |
| Fosetyl-Al + | 3 | 3.75 | May | 10 | 88.3 | 9.2 |
| Fosetyl-Al | 1 | 3.75 | AH |  |  |  |
| Benzothiadiazole + | 3 | 0.2 | May | 10 | 71.2 | 22.5 |
| Benzothiadiazole | 3 | 0.2 | June | 14 |  |  |
| Potassium phosphonate | 3 | 3 | May | 10 | 89.5 | 7.2 |
| Potassium phosphonate | 3 | 11.25 | May | 10 | 92.4 | 4.8 |

AH: after treatment

The results are calculated according to the following formula:

$$\text{Residue total (mg/kg)} = \text{Residue fosetyl-Al (mg/kg)} + \frac{M \text{ fosetyl-Al} \times \text{Residue phosphorous acid (mg/kg)}}{3 \times M \text{ phosphorous acid}}$$

in which:

$M_{fosetyl-Al}$ represents the molecular weight of fosetyl-Al: 354.1 g/mol $M_{phosphorous\ acid}$ represents the molecular mass of phosphorous acid: 82 g/mol; multiplied by 3, since 1 mol of fosetyl-Al corresponds to 3 mol of phosphorous acid.

For the pear bud samples, the fosetyl-Al and phosphorous acid residues are extracted with the aid of an acetonitrile/water (50:50, v/v) mixture. After centrifugation and dilution of the sampling material, the residues are quantified by HPLC and detected by tandem mass spectrometry with electrospray ionization. The quantification is performed by external standardization. The statistical analysis is performed per parameter on the complete set of data for the different sampling dates.

Results

Table 1 presents the percentage of flower buds of good quality as a result of the 2004 treatments. The following year, in 2005, 66% of the flower buds on the trees in the untreated control plot are well-developed normal buds with 5 to 7 flowers per bud and with rosette leaves around the flower buds. The data demonstrate that the two plots treated with phosphorous acid (having as origin fosetyl-Al or phosphorous acid itself) show a significantly increased flower bud Table 2 presents the percentage of good quality flower buds as a result of the 2004 and 2005 treatments. On 13 Feb. 2006, a first observation was made during the season of dormancy and at this time, the external qualities of the flower bud were comparable.

In 2006, during flowering, a second observation was made showing that 58% of the flower buds on the two-year wood were well-developed normal buds with 5 to 7 flowers per bud and leaves around the flower buds. In the plots treated with fosetyl-Al at 3×3.75 kg/ha in May or 6×3.75 kg/ha in May and June, the percentage of good quality flower buds increased to 86% and 92% respectively. Earlier during the primary flowering in 2005, the result of the position of the treatments with fosetyl-Al was a lower percentage of only 75% of good quality flower buds in 2006. A detailed evaluation of the quality of the flower bud on the various ages of the fruiting wood indicates that the reduced quality of flower bud is more frequent on the flower buds of the two-year old wood. On the one-year old wood in the side position and in the terminal position, the quality of the flower bud may be less influenced by the treatments with fosetyl-Al. In 2006, the differences in flower bud quality observed at the beginning of the season led to a higher number of fruits per tree at the end of the season in the plots treated with fosetyl-Al in May or May-June (Table 3). The results were a higher productivity in kg per tree.

TABLE 2

Formation of the 2006 flower bud as a result of the treatments performed in 2004 and 2005 on the tree and on the branches with separate evaluation of the branches of the 2-year old wood (2 yw) and on the 1-year old wood in the side position (1 yw S) and terminal position (1 yw T)

|  | Number of treatments | Dose (kg/ha) | Time of application | Interval | Good quality buds (%) | | | |
|---|---|---|---|---|---|---|---|---|
|  |  |  |  |  | Per tree | 2 yw | 1 yw S | 1 yw T |
| Not treated | / | / | / | / | 58 | 53.1 | 57.4 | 75.4 |
| Fosetyl-Al | 3 | 3.75 | May | 10 | 85.9 | 75.1 | 56.5 | 82.7 |
| Fosetyl-Al + | 3 | 3.75 | May | 10 | 92.3 | 86.1 | 68.4 | 97.2 |
| Fosetyl-Al | 3 | 3.75 | June | 14 |  |  |  |  |
| Fosetyl-Al | 3 | 3.75 | May | Primary efflorescence | 75.4 | 68.2 | 69.8 | 90.2 |
| Benzothiadiazole + | 3 | 0.2 | May | 10 | 62.8 | 58.5 | 56.6 | 54.6 |
| Benzothiadiazole | 3 | 0.2 | June | 14 |  |  |  |  |

TABLE 3

Productivity of the 2006 pear trees as a result of the treatments performed in 2004 and 2005

|  | Number of treatments | Dose (kg/ha) | Time of application | Interval | Number of fruits/tree | Productivity (kg/tree) | Average weight (g) |
|---|---|---|---|---|---|---|---|
| Not treated | / | / | / | / | 117.3 | 19.7 | 170.2 |
| Fosetyl-Al | 3 | 3.75 | May | 10 | 148.8 | 21.5 | 144.8 |
| Fosetyl-Al + | 3 | 3.75 | May | 10 | 152.2* | 21* | 137.9* |
| Fosetyl-Al | 3 | 3.75 | June | 14 |  |  |  |
| Fosetyl-Al | 3 | 3.75 | May | Primary efflorescence | 140.4 | 22.1 | 157.7 |
| Benzothiadiazole + | 3 | 0.2 | May | 10 | 113.88 | 18.5 | 163.2 |
| Benzothiadiazole | 3 | 0.2 | June | 14 |  |  |  |

*object excluded from statistical analysis

Table 4 presents the percentages of well-developed flower buds that have died back or that are incomplete in 2007 as a result of the treatments performed in 2006. A well-developed flower bud contained 5 to 7 flowers per cluster in the presence of well-developed leaves around the cluster. An incomplete bud contained only 2 to 3 flowers per cluster without the presence of leaves around the cluster. In the untreated plot, well-developed flower buds. The percentages of flower buds that have died back or that are incomplete were significantly reduced in all the objects treated with fosetyl-Al with no clear differences between the various application schemes. This means that the result of the various applications of fosetyl-Al in the post-flower period in 2006 was a large increase in the quality of flower bud in 2007.

TABLE 4

Formation of the 2007 flower bud as a result of the treatments performed in 2006

|  | Number of treatments | Dose (kg/ha) | Time of application | Interval | Good quality buds (%) | Buds that have died back (%) | Number of incomplete buds/tree |
|---|---|---|---|---|---|---|---|
| Not treated | / | / | / | / | 44.7 | 41.1 | 14.4 |
| Fosetyl-Al | 3 | 3.75 | May | 10 | 59.3 | 33.4 | 7.2 |
| Fosetyl-Al | 6 | 2 | May | 5 | 59.6 | 33 | 7.4 |
| Fosetyl-Al | 3 | 3.75 | June | 10 | 62.5 | 31.6 | 5.9 |
| Fosetyl-Al | 6 | 2 | June | 5 | 63.5 | 31.5 | 5 |
| Fosetyl-Al | 6 | 2 | May-June | 10 | 61.2 | 33.9 | 4.9 |
| Benzothiadiazole | 3 | 0.2 | May | 10 | 44.2 | 43.5 | 12.3 |

44.7 flower buds are well developed. The treatments with fosetyl-Al, in May at 3×3.75 kg/ha with an interval of 10 days or at 6×2 kg/ha with an interval of 5 days, increased the percentage of well-developed flower buds to 59%. The treatments with fosetyl-Al, in June at 3×3.75 kg/ha with an interval of 10 days or at 6×2 kg/ha with an interval of 5 days, increased the percentage of well-developed flower buds to 62.5%, respectively 63.5%. The treatments with fosetyl-Al repeated at 6×2 kg/ha applied during the May-June period with an interval of 10 days led to a percentage of 61.2% of well-developed flower buds.

Tables 5a, 5b, 5c present the levels of phosphorous acid and fosetyl-Al residues and the total residue measured in the flower buds during the 2006 season for the control untreated plot compared with the plot treated with fosetyl-Al at 3×3.75 kg/ha with an interval of 10 days in May and the plot treated with fosetyl-Al at 6×2 kg/ha with an interval of 10 days in May and in June. The samples were collected on the following dates: 30 May, 8 Jun., 19 Jun., 28 Jun., 10 Jul. and 28 Aug. 2006. The samples of pear tree buds were collected before the treatments.

TABLE 5a

Phosphorous acid residue in mg/kg per sampling date

| | Time of application and interval | 30/05 | 08/06 | 19/06 | 28/06 | 10/07 | 28/08 |
|---|---|---|---|---|---|---|---|
| Not treated | / | | 2.83 | 10.35 | 2.53 | 2.9 | 2.05 | 2.23 |
| Fosetyl-Al 3 × 3.75 kg/ha | May 10 days | 19.6 | 72.68 | 93.7 | 52.48 | 23.55 | 8.4 |
| Fosetyl-Al 6 × 2 kg/ha | May-June 10 days | 16.13 | 53.3 | 42.55 | 75 | 51.88 | 10.35 |

TABLE 5b

Fosetyl-Al residue in mg/kg per sampling date

| | Time of application and interval | 30/05 | 08/06 | 19/06 | 28/06 | 10/07 | 28/08 |
|---|---|---|---|---|---|---|---|
| Not treated | / | 0.1 | 4.83 | 0.25 | 0.83 | 0.12 | 0.1 |
| Fosetyl-Al 3 × 3.75 kg/ha | May 10 days | 0.1 | 12.92 | 10.65 | 10.83 | 2.14 | 0.11 |
| Fosetyl-Al 6 × 2 kg/ha | May-June 10 days | 0.1 | 10.64 | 4.52 | 20.56 | 2.86 | 0.18 |

TABLE 5c

Total (fosetyl-Al + phosphorous acid) residue in mg/kg per sampling date

| | Time of application and interval | 30/05 | 08/06 | 19/06 | 28/06 | 10/07 | 28/08 |
|---|---|---|---|---|---|---|---|
| Not treated | / | | 4.18 | 19.73 | 3.88 | 5.01 | 3.08 | 3.32 |
| Fosetyl-Al 3 × 3.75 kg/ha | May 10 days | 28.31 | 117.53 | 145.53 | 86.37 | 36.04 | 12.18 |
| Fosetyl-Al 6 × 2 kg/ha | May-June 10 days | 23.3 | 87.36 | 65.76 | 128.61 | 77.53 | 15.1 |

Discussion

The results of the evaluation of the quality of the flower bud indicate that there is an obvious increase in the quality of the flower bud in the objects treated with phosphonate (fosetyl-Al or phosphorous acid).

A combination of factors may come into play during this phenomenon: for example bacterial infections caused by *Pseudomonas syringae* pv *syringae* or by *Pantoaea* sp (not systematically isolated in the pear tree buds); fungal infections caused by *Alternaria alternata*; climatological influences.

During these trials, the best period for applying the fosetyl-Al treatments in order to solve the problem of flower buds that have died back on the pear tree is the post-flower period. It is the period during which the flower buds on the two-year old wood are formed. It has been found to be important to improve the plant resistance during the early stage of the development of the flower bud. The systemic characteristic of the fosetyl-Al product may also constitute an important aspect for the penetration of the product into the leaves around the developing meristems inside the flower buds on the two-year old wood.

During the 2006 trial, the residual levels of phosphorous acid and fosetyl-Al in the developing flower buds were monitored. The flower bud samples were collected before the following treatment. The data indicate that after the treatments, a substantial increase is observed in the phosphorous acid content in the flower buds. There is a clear difference between the object with a higher dose after treatment with fosetyl-Al at 3×3.75 kg/ha and the object with treatments with fosetyl-Al at a repeated lower dose of 2 kg/ha. In the first object, the phosphonate residue increases after the last treatment and approximately 4 weeks are required before the residue falls below the value of 30 mg/kg. In the object with the repeated lower doses of 2 kg/ha, approximately 2 weeks are required after the last treatment for the residue to fall below 30 mg/kg. Furthermore, the level of fosetyl-Al residue was maintained for about 4 weeks after the last treatment with fosetyl-Al at a dose of 3.75 kg/ha. The residual level of phosphorous acid during the period of formation of the flower buds on the two-year old wood is maintained in the plant.

CONCLUSION

The repeated treatments with fosetyl-Al on the pear trees in the post-flower period significantly improved the quality of the flower buds for the following year. A repeated dose of 3×3.75 kg/ha, applied in the post-flower period with an interval of 10 days, is the most advantageous.

The residual effect of the treatments with fosetyl-Al on the content of phosphorous acid inside the flower buds up to four weeks after the last treatment is also particularly advantageous.

The invention claimed is:

1. A method for improving the quality of flower buds of a perennial fruit crop plant comprising applying a compound selected from the group consisting of phosphorous acid, a salt of phosphorous acid, fosetyl-aluminum, fosetyl-calcium, and fosetyl-sodium to said plant at a time of initiation of the flower buds in a post-flower period, wherein the flower buds of said plant are not infested by bacterial infections caused by *Pseudomonas syringae* pv. *syringae* and wherein the application of the compound is repeated at least three times in a quantity of at least 1.5 kg/ha.

2. A method as claimed in claim 1, wherein the compound is selected from the group consisting of phosphorous acid and fosetyl-Al.

3. A method as claimed in claim 1, wherein the compound is applied starting at a time of initiation of the flower bud of a plant to be treated.

4. A method as claimed in claim 1, wherein the compound is applied at a time of initiation of the flower bud and of cell multiplication in flower buds of a plant to be treated.

5. A method as claimed in claim 1, wherein the application of the compound stops approximately 10 weeks after having started.

6. A method as claimed in claim 1, wherein the application of the compound stops approximately 8 weeks after having started.

7. A method as claimed claim 1, wherein application of the compound is applied in a quantity to obtain a concentration in the plant of at least 15 ppm.

8. A method as claimed in claim 1, wherein the compound is applied in a quantity to obtain a concentration in the plant of at least 30 ppm.

9. A method as claimed in claim 1, wherein fosetyl-Al or phosphorous acid is applied in a quantity of at least 3 kg/ha.

10. A method as claimed in claim 1, wherein the plant comprises fruit crops, pome fruit crops, stone fruit crops, horticultural, tree or forestry crops.

11. A method as claimed in claim 1, wherein the plant comprises apple trees, pear trees, apricot trees, cherry trees, plum trees, sour cherry trees, almond trees, or peach trees.

12. A method as claimed in claim 1, wherein fosetyl-Al or phosphorous acid is applied in a quantity of at least 2 kg/ha.

13. A method as claimed in claim 1, wherein the compound is fosetyl-Al.

14. A method as claimed in claim 1, wherein fosetyl-Al is applied in a quantity of at least 2 kg/ha.

15. A method as claimed in claim 1, wherein the application of the compound is repeated three to six times.

\* \* \* \* \*